(12) United States Patent
Raksi et al.

(10) Patent No.: US 7,611,507 B2
(45) Date of Patent: Nov. 3, 2009

(54) DISPOSABLE PATIENT INTERFACE

(75) Inventors: Ferenc Raksi, Irvine, CA (US); Tibor Juhasz, Irvine, CA (US); Ron Kurtz, Irvine, CA (US); Wes Lummis, San Clemente, CA (US); Chris Davis, San Marcos, CA (US); Laszlo Nagy, Anaheim Hills, CA (US)

(73) Assignee: AMO Development LLC, Santa Ana, CA (US)

( * ) Notice: Subject to any disclaimer, the term of this patent is extended or adjusted under 35 U.S.C. 154(b) by 672 days.

(21) Appl. No.: 11/258,399

(22) Filed: Oct. 24, 2005

(65) Prior Publication Data

US 2007/0093796 A1    Apr. 26, 2007

(51) Int. Cl.
*A61F 9/007* (2006.01)

(52) U.S. Cl. .................................. 606/4; 606/5; 606/6
(58) Field of Classification Search .................. 606/4–6
See application file for complete search history.

(56) References Cited

U.S. PATENT DOCUMENTS

| | | | | |
|---|---|---|---|---|
| 4,905,711 | A * | 3/1990 | Bennett et al. | 128/869 |
| 5,009,660 | A | 4/1991 | Clapham | 606/166 |
| 5,102,409 | A * | 4/1992 | Balgorod | 606/5 |
| 5,141,506 | A * | 8/1992 | York | 606/5 |
| 5,171,254 | A | 12/1992 | Sher | 606/166 |
| 5,282,088 | A | 1/1994 | Davidson | 359/664 |
| 5,336,215 | A * | 8/1994 | Hsueh et al. | 606/4 |
| 5,359,373 | A | 10/1994 | Koester et al. | 351/219 |
| 5,490,849 | A * | 2/1996 | Smith | 606/5 |
| 5,549,632 | A | 8/1996 | Lai | 606/5 |
| 5,556,417 | A | 9/1996 | Sher | 600/236 |
| 5,807,379 | A | 9/1998 | L'Esperance, Jr. et al. | 606/5 |
| 5,984,915 | A | 11/1999 | Loeb et al. | 606/9 |
| 5,984,916 | A | 11/1999 | Lai | 606/5 |
| 5,997,559 | A | 12/1999 | Ziemer | 606/166 |
| 6,134,042 | A | 10/2000 | Dhuler et al. | 250/208.1 |
| 6,156,028 | A | 12/2000 | Prescott | |
| 6,247,473 | B1 | 6/2001 | Yavitz | 128/899 |
| 6,254,595 | B1 | 7/2001 | Juhasz et al. | 606/5 |
| 6,325,792 | B1 | 12/2001 | Swinger et al. | 606/4 |
| 6,373,571 | B1 | 4/2002 | Juhasz et al. | 356/399 |
| 6,436,113 | B1 | 8/2002 | Burba et al. | 606/166 |

(Continued)

FOREIGN PATENT DOCUMENTS

WO    WO/01/44871    6/2001

OTHER PUBLICATIONS

Mitsutoshi Ito et al.: "Picosecond Laser in Situ Keratomileusis With a 1053-nm Nd: YLF Laser", Journal of Refractive Surgery vol. 12 Sep./Oct. 1996.

(Continued)

*Primary Examiner*—Henry M Johnson, III
*Assistant Examiner*—Ronald Hunter

(57) ABSTRACT

A patient interface device adapted to provide an interface between a cornea and a surgical laser system. A frame has an applanation end and an attachment end which is adapted to couple to the surgical laser system. A skirt is affixed to the applanation end of the frame and is adapted to seal against the anterior surface of the cornea to form a chamber. A lens is disposed near the applanation end of the frame and is supported by a flexible support which affixes the lens to the frame.

20 Claims, 3 Drawing Sheets

U.S. PATENT DOCUMENTS

| | | | |
|---|---|---|---|
| 6,623,476 B2 | 9/2003 | Juhasz et al. | 606/5 |
| 6,676,653 B2 | 1/2004 | Juhasz et al. | 606/4 |
| 6,863,667 B2 | 3/2005 | Webb et al. | 606/4 |
| 6,899,707 B2 | 5/2005 | Schroller et al. | 606/5 |
| 2002/0103481 A1* | 8/2002 | Webb et al. | 606/5 |
| 2005/0143718 A1 | 6/2005 | Rathjen | 606/5 |
| 2007/0093796 A1* | 4/2007 | Raksi et al. | 606/10 |

OTHER PUBLICATIONS

Tabor Juhasz, Frieder H.Loesel, Ron M. Kurtz, Christopher Horvath, Josef F. Bille and Berard Mourou, Corneal Refractive Surgery with Femtosecond Laser, IEEE Journal of Selected Topic in Quantum Electronics, vol. 5, No. 4, Jul./Aug. 1999.

* cited by examiner

DISPOSABLE PATIENT INTERFACE

BACKGROUND OF THE INVENTION

1. Field of the Invention

The field of the present invention is patient interface devices for use with opthalmic surgical laser systems.

2. Background

Many advances have been made in the area of ophthalmic surgery in recent years. In particular, lasers are being used more and more frequently to perform certain ophthalmic surgical procedures. One important aspect of such procedures is accurate positioning of the eye in relationship to the laser system, thereby allowing the laser beam to be directed with a high degree of accuracy. Accuracy in directing the laser beam during ophthalmic surgical procedures is important because an inaccurately or improperly directed laser beam could cause permanent damage to the eye.

One method of positioning the eye relative to the laser beam is to use a contact lens to stabilize the eye. This method, however, requires the contact lens itself to be accurately aligned with respect to the laser source, and therefore does not satisfactorily solve the alignment problem.

Another option for maintaining alignment between the eye and the laser source is to permanently mount the lens to the exit aperture of the laser system. However, with the contact lens permanently mounted on the laser system, the lens would require sterilization following each surgical procedure. Alternatively, the lens could be replaced following each procedure, but such an option introduces the need to align each replacement contact with the exit aperture before the system could be used. In either case, additional time and costs would be added to each procedure.

Alternative methods of providing accurate alignment are also known.] U.S. Pat. No. 5,549,632 to Lai, the disclosure of which is incorporated herein by reference, describes an apparatus for controlling the shape of the cornea during ophthalmic surgery. A transparent applanator plate is placed in contact with the cornea of a patient's eye. The applanator plate creates a fixed positional frame of reference which the laser beam control system can use to position the focus of the laser beam. A surgical tip at the distal end of an articulated arm having flexible joints is placed in contact with the applanator plate and follows any motion of the patient's eye and directs the laser beam to the surgical tip. The applanator plate also provides a means to control the contour of the index of refraction boundary between the corneal epithelium of the patient's eye and the air.

Various types of disposable contact lenses for use with ophthalmic laser systems are also known. For example, U.S. Pat. No. 6,254,595 to Juhasz et al., the disclosure of which is incorporated herein by reference, describes a disposable applanatic lens for use during ophthalmic laser surgery. The disposable applanatic lens includes a lens which has a flat anterior surface which is substantially parallel to a flat applanation surface. A skirt surrounds the applanation surface and extends outwardly therefrom to define a chamber. Additionally, the skirt includes a vacuum channel which is formed about the applanation surface. During procedures, contact between the skirt and the cornea encloses the vacuum channel. A vacuum pump is in fluid communication with the enclosed vacuum channel and is employed during the surgical procedure to at least partially evacuate the vacuum channel, thereby sealing the skirt against the cornea.

U.S. Pat. No. 6,373,571 to Juhasz et al., the disclosure of which is incorporated herein by reference, describes a disposable contact lens and an adjustable retainer ring for mounting the contact lens on the laser system. In order to properly align the disposable contact lens to the laser system, reference marks on the contact lens are brought into coincidence with predetermined focal points along the laser beam paths.

SUMMARY OF THE INVENTION

The present invention is directed toward a patient interface device which stabilizes the eye and provides an interface between the eye and an opthalmic surgical laser system during laser opthalmic surgery. The frame of the patient interface device has an applanation end and an attachment end. The attachment end is adapted to couple with the surgical laser system. A skirt is affixed to the applanation end of the frame and is adapted to seal against the anterior surface of the cornea to form a chamber. A lens is disposed near the applanation end of the frame and is affixed to the frame by a flexible support.

Optionally, the patient interface device may be configured as a biological barrier. The flexible support may be annular in shape and constructed to act as a biological barrier between the eye and the opthalmic surgical laser system. With such a configuration, the frame may be constructed of perforated sidewalls to form the cavity. The attachment end of the frame may also be adapted to seal against the opthalmic surgical laser system to provide a further biological barrier. As another, the applanation end of the frame may include one or more vent ports. Such vent ports help eliminate relative pressure changes of air or fluids trapped between the cornea and the flexible biological barrier and lens.

Accordingly, the present invention provides an improved patient interface device for use opthalmic surgical laser systems. Other objects and advantages will appear hereinafter.

BRIEF DESCRIPTION OF THE DRAWINGS

In the drawings, wherein like reference numerals refer to similar components.

DETAILED DESCRIPTION OF THE PREFERRED EMBODIMENTS

Figure 1:
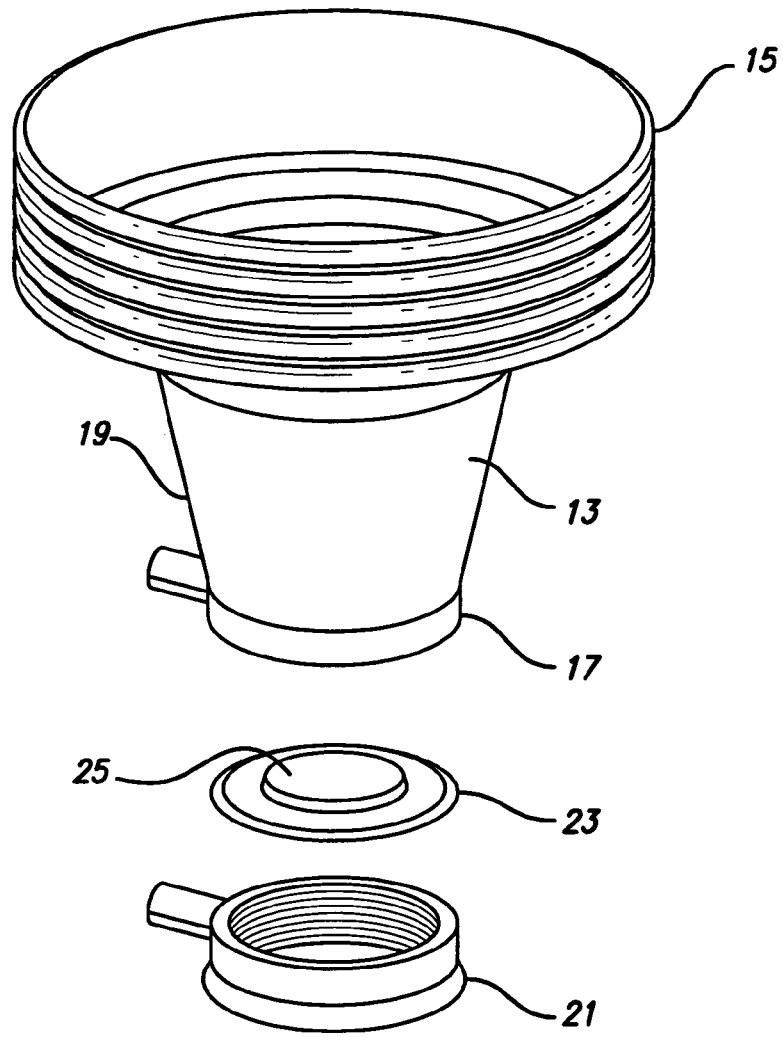
FIG. 1 is an exploded perspective view of a patient interface device.

Turning in detail to the drawings, FIG. 1 illustrates a patient interface device 11 which is adapted to interface between a opthalmic surgical laser system (not shown) and the cornea of an eye (not shown). The frame 13 of the patient interface device 11 has an attachment end 15 and an applanation end 17. The attachment end 15 is broad and open to accommodate the exit aperture of an ophthalmic surgical laser system, while the applanation end 17 is considerably narrower to facilitate the coupling between the device 11 and the eye during a surgical procedure. Between the attachment end 15 and the applanation end 17, the sidewalls 19 of the frame 13 form a conical cavity. The shape of the frame 13, however, is generally a matter of design choice. The frame 13 also has non-perforated sidewalls 19. The lack of perforations in the sidewalls 19 helps reduce the chances of cross contamination between the eye and the opthalmic surgical laser system during a surgical procedure. However, a more open frame may be suitable if sidewall perforations are located such that the sterile barrier is maintained between the eye and the opthalmic surgical laser system.

Figure 2:
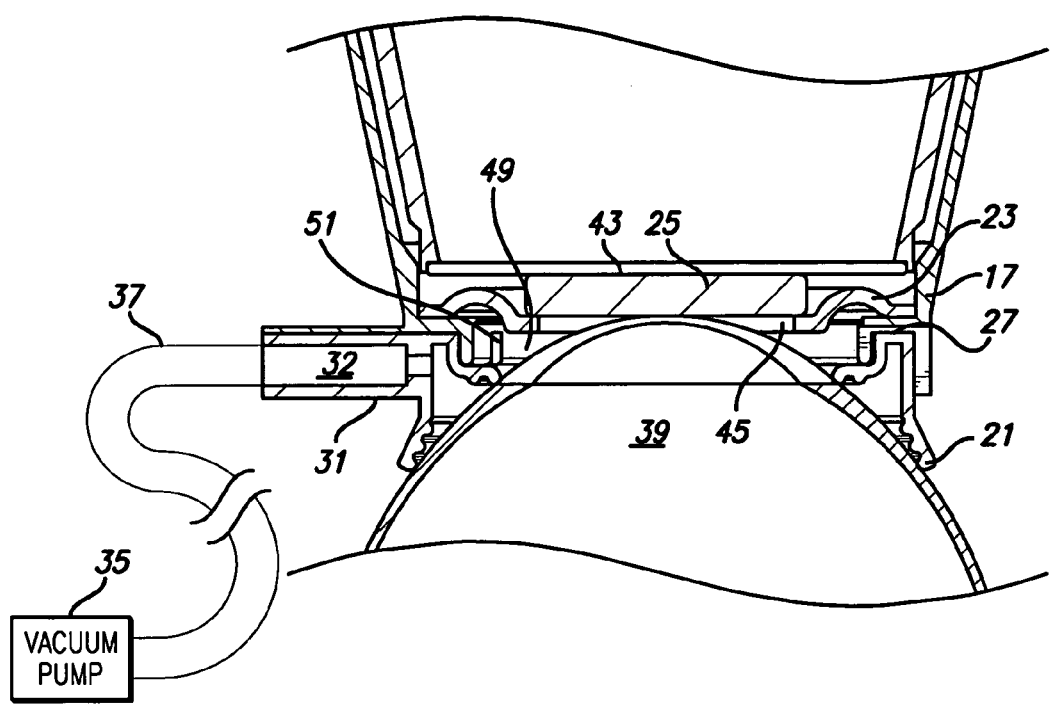
FIG. 2 is a cross-sectional detailed view of the applanation end of a patient interface device.

An annular skirt 21, an annular flexible support 23, and a lens 25 are affixed to the applanation end 17 of the frame 13, with the skirt 21 and the flexible support 23 being affixed directly to the frame 13, and the lens 25 being affixed directly to the flexible support 23. The details of the applanation end 17 of the frame 13 are illustrated in FIG. 2. The annular skirt 21 is seated in a complimentary annular channel 27 in the applanation end 17 of the frame 13. The channel 27 includes an arm 31 which extends from the skirt 21. The arm 31 houses a passageway 32 which may be affixed to a vacuum pump 35 through a tube 37. The vacuum pump 35 may be a syringe or any other mechanical device capable of generating negative pressure. The patient interface device 11 is employed to immobilize the eye during surgery. For this purpose, the skirt 21 is preferably constructed of a soft, pliable material. When the skirt 21 is placed against the eye 39, a chamber 49 is formed and the vacuum pump 35 may be used to create at least a partial vacuum within the chamber, thereby coupling the skirt 21, and thus the patient interface device 11, to the eye 39.

The skirt 21 is preferably affixed to the applanation end 17 of the frame 13 using an adhesive which is appropriate for the materials used. Such an adhesive should be one that will not quickly deteriorate when exposed to light from lasers generally employed in opthalmic surgical laser systems.

The lens 25 has a posterior surface 43 and an anterior surface 45, and may be planar, as shown, or one or both of the surfaces may be curved. The outer edge of the anterior surface 45 is adhered to the flexible support 23. Again, the adhesive may be any that is appropriate for the materials used, with consideration for the laser light to which the adhesive will be exposed. As is understood in the relevant art, the anterior surface 45 of the lens 25 makes contact with the cornea during the surgical procedure and flattens, configures, or otherwise shapes the cornea for the surgical procedure. The geometrical configuration of the lens 25 therefore depends upon the shape to which the cornea is to be conformed during the surgical procedure. The lens 25 is preferably made of a inexpensive high strength transparent material, such as glass, plastic, or the like.

The flexible support 23 is itself adhered to the applanation end 17 of the frame 13 using an adhesive, although a mechanical coupling could also be used. The considerations for the adhesive are again the same.

During ophthalmic laser surgery, a secondary chamber 49 is created when the patient interface device 11 is coupled to the eye 39. The secondary chamber 49 is formed by the anterior surface 45 of the lens 25, the flexible support 23, the annular channel 27 of the frame 13, the annular skirt 21, and the cornea of the eye 39. The volume of the secondary chamber 49 changes as the lens 25 moves on the flexible support. The amount of lens movement is an important factor in determining the amount by which the cornea is flattened, configured, or otherwise shaped for the surgical procedure. As the volume of the secondary chamber 49 changes, a localized change of pressure occurs within the pocket. This pressure change can negatively affect the ability to shape the cornea as desired using the lens 25. To alleviate this problem, vent ports 51 are disposed within the applanation end 17 of the frame 13. The vent ports 51 permit the relative pressure of air or fluids within the secondary chamber 49 to equalize to atmospheric pressure. The vent ports 51 preferably do not compromise the sterile barrier between the eye 39 and the ophthalmic surgical laser system, nor do they compromise the established pressure within the vacuum chamber 41. The patient interface device 11 may include a single vent port, or up to twelve or more vent ports. Multiple vent ports are preferably regularly spaced in a ring about an axis perpendicular to the lens 25.

The vent ports 51 help ensure that the shape of the cornea is dictated solely by pressure upon the posterior surface 43 of the lens 25.

Figure 3:
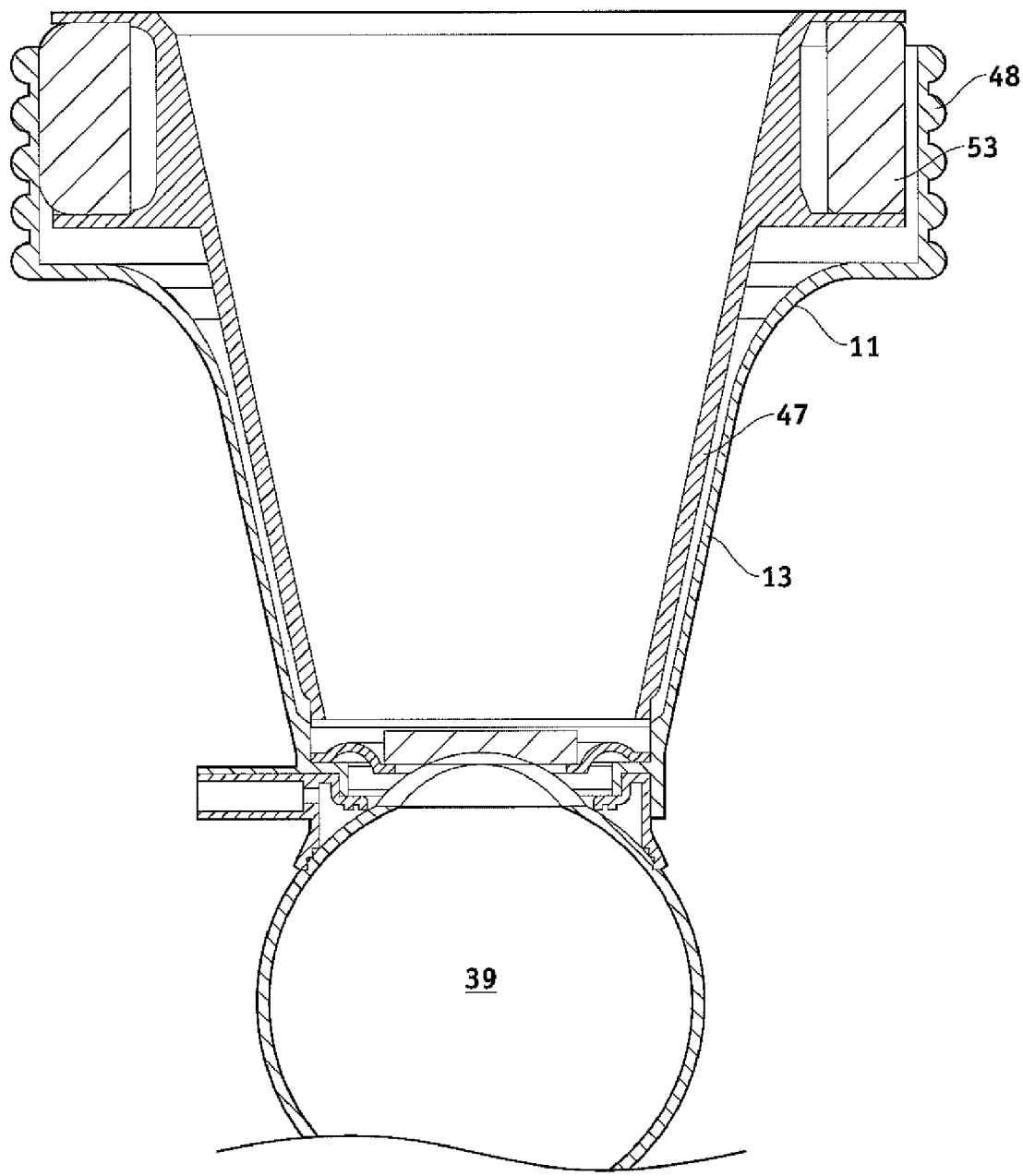
FIG. 3 is a cross-sectional view of a patient interface device as employed to interface between a opthalmic surgical laser system and an eye.

FIG. 3 illustrates the patient interface device 11 providing an interface between the patient's eye 39 and the exit aperture housing 47 of the opthalmic surgical laser system. The frame 13 of the patient interface device 11 is configured to have a complimentary shape to the exit aperture housing 47. This allows the exit aperture housing 47 to be inserted directly into the frame 13 and be positioned immediately adjacent the eye 39 without being in physical contact with the eye 39, thereby facilitating the surgical procedure while reducing opportunities for cross contamination between the eye and the exit aperture housing 47.

The attachment end 15 of the frame 13 is coupled to the exit aperture housing 47 to further reduce opportunities for cross contamination and to stabilize the interface. This coupling may be achieved by inclusion of a ferromagnetic material in rings 48 circumscribing the attachment end 15 of the frame 13 and complimentary sliding electromagnets 53 in the exit aperture housing 47. The electromagnets 53 are slidable in a radial direction so that when activated, they may couple with, and seal against the attachment end 15 of the frame 13. Alternative methods of coupling the frame 13 to the exit aperture housing 47 may also be employed, including one or more mechanical latches, an inflatable bladder, and the like.

Thus, an improved patient interface device for use with ophthalmic surgical laser systems is disclosed. While embodiments of this invention have been shown and described, it will be apparent to those skilled in the art that many more modifications are possible without departing from the inventive concepts herein. The invention, therefore, is not to be restricted except in the spirit of the following claims.

What is claimed is:

1. A patient interface device adapted to provide an interface between a cornea and a surgical laser system, the device comprising:
    a frame having an applanation end and an attachment end, wherein the attachment end is adapted to couple to the surgical laser system;
    a skirt affixed to the applanation end of the frame, wherein the skirt is adapted to seal against an anterior surface of the cornea to form a chamber;
    a lens disposed near the applanation end of the frame; and
    a flexible support affixing the lens to the frame.

2. The device of claim 1, wherein the attachment end comprises non-perforated sidewalls.

3. The device of claim 2, wherein the sidewalls form a conical cavity.

4. The device of claim 1, wherein the applanation end of the frame includes a vent port.

5. The device of claim 1, wherein the flexible support comprises a biological barrier.

6. The device of claim 1, wherein the flexible support is annular.

7. The device of claim 6, wherein the lens is centered on the annular flexible support.

8. The device of claim 1, wherein the attachment end is adapted to couple to the surgical laser system.

9. The device of claim 1, wherein the attachment end comprises a ferromagnetic material.

10. The device of claim 1 further comprising a vacuum pump in fluid communication with the chamber.

11. The device of claim 1, wherein the skirt is annular.

12. A patient interface device adapted to provide an interface between a cornea and a surgical laser system, the device comprising:
- a frame having an applanation end and an attachment end, wherein the attachment end includes non-perforated sidewalls and the attachment end is adapted to couple to the surgical laser system, and wherein the applanation end includes a vent port;
- a skirt affixed to the applanation end of the frame, wherein the skirt is adapted to seal against an anterior surface of the cornea to form a chamber, the vent port not in fluid communication with the chamber;
- a lens disposed near the applanation end of the frame; and
- a flexible biological barrier affixing the lens to the frame.

13. The device of claim 12, wherein the sidewalls form a conical cavity.

14. The device of claim 12, wherein the biological barrier is annular.

15. The device of claim 14, wherein the lens is centered upon the annular biological barrier.

16. The device of claim 12, wherein the attachment end includes a ferromagnetic material.

17. The device of claim 12 further comprising a vacuum pump in fluid communication with the chamber.

18. The device of claim 12, wherein the skirt is annular.

19. A patient interface device adapted to provide an interface between a cornea and a surgical laser system, the device comprising:
- a frame having an applanation end and an attachment end, the attachment end is adapted to couple to the surgical laser system, and the applanation end includes at least one vent port;
- an annular skirt affixed to the applanation end of the frame, wherein the skirt is adapted to seal against an anterior surface of the cornea to form a first chamber;
- a lens disposed near the applanation end of the frame;
- an annular, flexible biological barrier affixing the lens to the frame, wherein the lens is centered upon the biological barrier; and
- a vacuum pump in fluid communication with the first chamber;
- wherein the lens, the biological barrier, the anterior surface of the cornea, the applanation end, and the skirt form a second chamber in fluid communication with the at least one vent port, the second chamber having a volume varying as the lens displaces on the biological barrier.

20. The device of claim 19, wherein the attachment end includes a ferromagnetic material.

* * * * *

UNITED STATES PATENT AND TRADEMARK OFFICE
CERTIFICATE OF CORRECTION

PATENT NO.        : 7,611,507 B2                                         Page 1 of 1
APPLICATION NO.   : 11/258399
DATED             : November 3, 2009
INVENTOR(S)       : Raksi et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1000 days.

Signed and Sealed this

Twelfth Day of October, 2010

David J. Kappos
*Director of the United States Patent and Trademark Office*